(12) United States Patent
Baur

(10) Patent No.: US 8,535,015 B2
(45) Date of Patent: Sep. 17, 2013

(54) RINSING DEVICE AND METHOD FOR THE OPERATION THEREOF

(75) Inventor: Thomas Baur, Rottenburg (DE)

(73) Assignee: Erbe Elektromedizin GmbH, Tübingen (DE)

(*) Notice: Subject to any disclaimer, the term of this patent is extended or adjusted under 35 U.S.C. 154(b) by 0 days.

(21) Appl. No.: 13/237,635

(22) Filed: Sep. 20, 2011

(65) Prior Publication Data

US 2012/0006415 A1    Jan. 12, 2012

Related U.S. Application Data

(62) Division of application No. 11/570,055, filed as application No. PCT/EP2005/006201 on Jun. 9, 2005, now Pat. No. 8,038,414.

(30) Foreign Application Priority Data

Jun. 11, 2004    (DE) .......................... 10 2004 028 361

(51) Int. Cl.
  *F04B 49/06*    (2006.01)
  *A61B 1/12*     (2006.01)

(52) U.S. Cl.
  USPC ....................................... 417/44.11; 600/156

(58) Field of Classification Search
  USPC .................. 417/12, 20, 43, 44.1, 44.2, 44.11; 604/67; 600/156, 159
  See application file for complete search history.

(56) References Cited

U.S. PATENT DOCUMENTS

| 4,998,914 | A  |   | 3/1991  | Wiest et al.           |
|-----------|----|---|---------|------------------------|
| 5,725,357 | A  | * | 3/1998  | Nakazeki et al. 417/18 |
| 5,736,823 | A  |   | 4/1998  | Nordby et al.          |
| 5,931,808 | A  |   | 8/1999  | Pike                   |
| 6,170,241 | B1 | * | 1/2001  | Shibilski et al. 56/11.9 |
| 6,375,653 | B1 | * | 4/2002  | Desai 606/41           |
| 2001/0039370 | A1 |   | 11/2001 | Takahashi et al.     |
| 2003/0138327 | A1 | * | 7/2003  | Jones et al. 417/42  |
| 2003/0139643 | A1 |   | 7/2003  | Smith et al.         |
| 2004/0097872 | A1 |   | 5/2004  | Delk et al.          |

FOREIGN PATENT DOCUMENTS

DE    25 35 650    2/1977

OTHER PUBLICATIONS

English translation of International Preliminary Report on Patentability issued by the International Bureau on Dec. 28, 2006.

* cited by examiner

*Primary Examiner* — Devon Kramer
*Assistant Examiner* — Bryan Lettman
(74) *Attorney, Agent, or Firm* — Dickstein Shapiro LLP

(57) ABSTRACT

A method of operating a rinsing pump, for example, a peristaltic roller pump for use in endoscopy, which involves reducing a rinsing fluid flow rate to a safe flow rate when a detected electrical current exceeds a first predetermined current value, in which the first predetermined current value corresponds to a first predetermined limiting rinsing pressure. The method in part prevents an excessively high pressure in case of an unintended stenosis, e.g., kinking of the supply tube, or also intended stenoses, e.g., insertion of a narrow rinsing probe, by detecting an electrical current received by the pump by a current-measuring device.

9 Claims, 2 Drawing Sheets

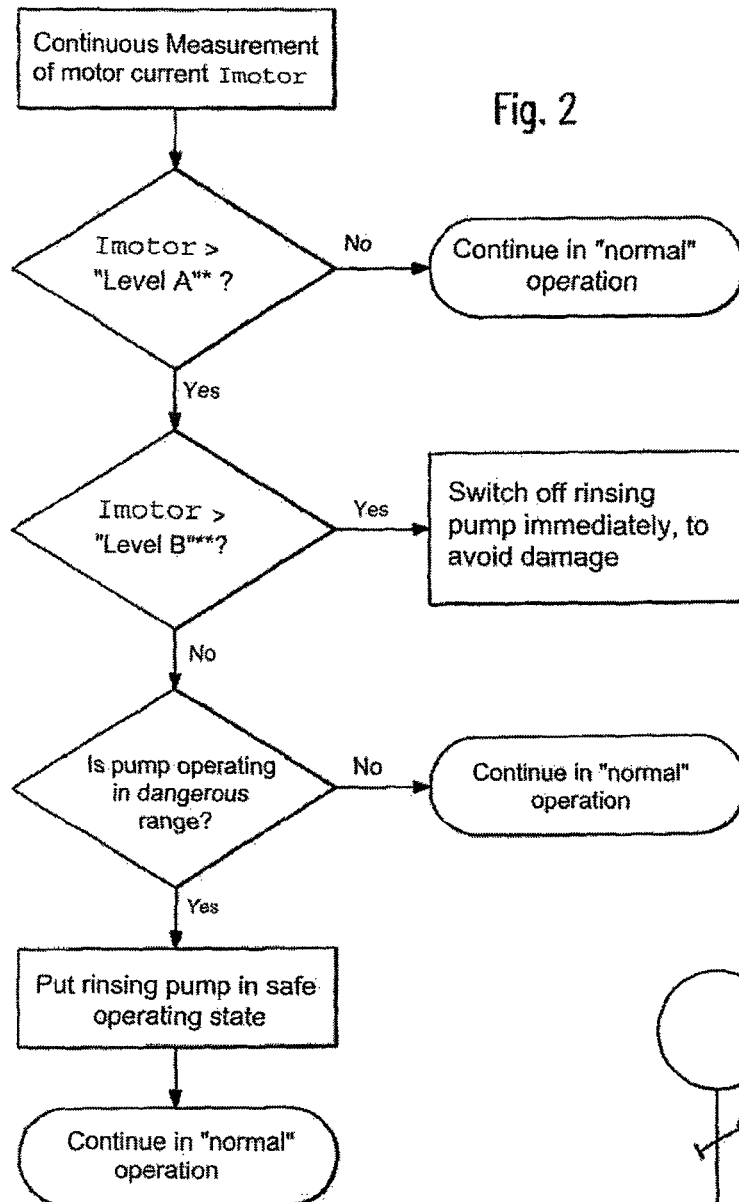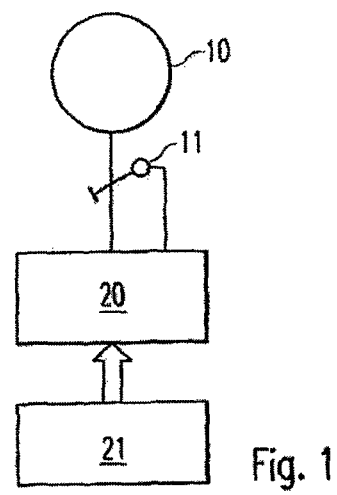

RINSING DEVICE AND METHOD FOR THE OPERATION THEREOF

CROSS-REFERENCE TO RELATED APPLICATIONS

This application is a divisional application of and claims priority to U.S. application Ser. No. 11/570,055, filed on Dec. 5, 2006, now U.S. Pat. No. 8,038,414, which is a Section 371 of International Application No. PCT/EP2005/006201, filed Jun. 9, 2005, which was published in the German language on Dec. 22, 2005 under International Publication No. WO/2005/120328, the disclosures of which are incorporated herein by reference.

BACKGROUND OF THE INVENTION

The invention relates to a rinsing device, in particular for endoscopy, as well as to a method for operating a rinsing device of this kind.

Rinsing devices used for medical purposes customarily comprise a peristaltic roller pump by means of which a rinsing fluid (e.g., Ringer solution) can be supplied to an applicator in order to carry out a rinsing process with no risk of contamination, for instance rinsing a region in which an operation is being performed. In endoscopy such rinsing devices are additionally used to clean optical components of the endoscope.

Problems arise with such rinsing devices in that stenoses can be produced, e.g. by clogging or bending the tube that conducts the fluid, which can result in breakage of the tube. This endangers the patient, and should absolutely be avoided.

Furthermore, such rinsing devices are employed in combination with a variety of applicators, depending on the site where they are used, which can likewise cause the tube to break, in particular when the rinsing probes are thin and the operator requires an excessive amount of fluid to be supplied.

BRIEF SUMMARY OF THE INVENTION

The present invention provides a rinsing device of the kind cited at the outset that can be automatically adjusted so as to operate reliably and a method of operating the rinsing device so that the problems described above are solved or substantially mitigated.

With regard to the apparatus, according to the present invention there is provided a rinsing device, in particular for endoscopy, which comprises an electrically driven pump, in particular a peristaltic roller pump, and a control device to detect and/or adjust a flow rate, such that a current-measuring device is provided to monitor an electrical current received by the pump and the control device is designed so that when the flow rate exceeds a prespecified limiting value and the current simultaneously exceeds a first prespecified current value, the flow rate is reduced to a safe flow-rate value.

The basis of the invention is without separate measurement of the rinsing pressure, i.e. solely by measuring the current and comparing the result with a threshold value for a known flow rate, the latter can be reduced to a non-injurious level if the current has increased. Even if a flow rate that has been set by the operator turns out to be too high for a thin rinsing probe (which has been attached by the operator), so that a dangerously high pressure would be produced, the danger is automatically and reliably avoided. That is, when the adjusted flow rate is below the safe value, breakage of the tube does not occur.

Preferably the control device is designed in such a way that the safe value for the flow rate is equal to or somewhat lower than the limiting value, so as to obtain a hysteresis. In any case, however, the flow rate is reduced far enough that there is no longer any danger.

The control device is preferably constructed in such a way that when the current exceeds a second prespecified current value that is higher than the first current value, the pump is (completely) turned off and/or a warning signal is generated. That is, such a high current value signifies that the motor is blocked (e.g., by problems at the rollers). This measure ensures protection of the rinsing device.

Once the flow rate has been reduced to the safe value as described above, in a preferred embodiment of the invention the flow rate is increased at a prespecified rate—stepwise, so to speak—until it corresponds to the desired flow rate that has been specified by the operator. If the current again exceeds the first prespecified current value, the flow rate is again reduced to the non-dangerous value. In case of a temporary stenosis of the tube, e.g. due to occasional compression or kinking, the result is that on one hand the tube does not burst, whereas on the other hand when the stenosis is no longer present the value desired by the operator is again reached.

Regarding the method, according to the present invention there is provided a method of operating a rinsing device in particular for endoscopy comprising an electrically driven pump, in particular a peristaltic roller pump, wherein a flow rate is detected and/or specified, a current received by the pump is detected, and the flow rate is then reduced to a safe value whenever the flow rate exceeds a prespecified limiting flow value and simultaneously the current exceeds a first prespecified current value. In this case the flow-rate safe value is equal to the limiting value.

Furthermore, whenever the current exceeds a second prespecified current value that is higher than the first current value, the pump is turned off and/or a warning signal is generated.

After the flow rate has been reduced to the safe value the flow rate is increased at a prespecified rate (stepwise) up to a prespecified desired flow rate.

Preferred embodiments of the invention will be apparent from the subordinate claims.

BRIEF DESCRIPTION OF THE SEVERAL VIEWS OF THE DRAWINGS

The foregoing summary, as well as the following detailed description of the invention, will be better understood when read in conjunction with the appended drawings. For the purpose of illustrating the invention, there are shown in the drawings embodiments which are presently preferred. It should be understood, however, that the invention is not limited to the precise arrangements and instrumentalities shown.

In the drawings:

FIG. 1 is a block diagram of an embodiment of the rinsing device,

FIG. 2 is a flow diagram to explain the reduction of the flow rate, and

DETAILED DESCRIPTION OF THE INVENTION

Figure 3:
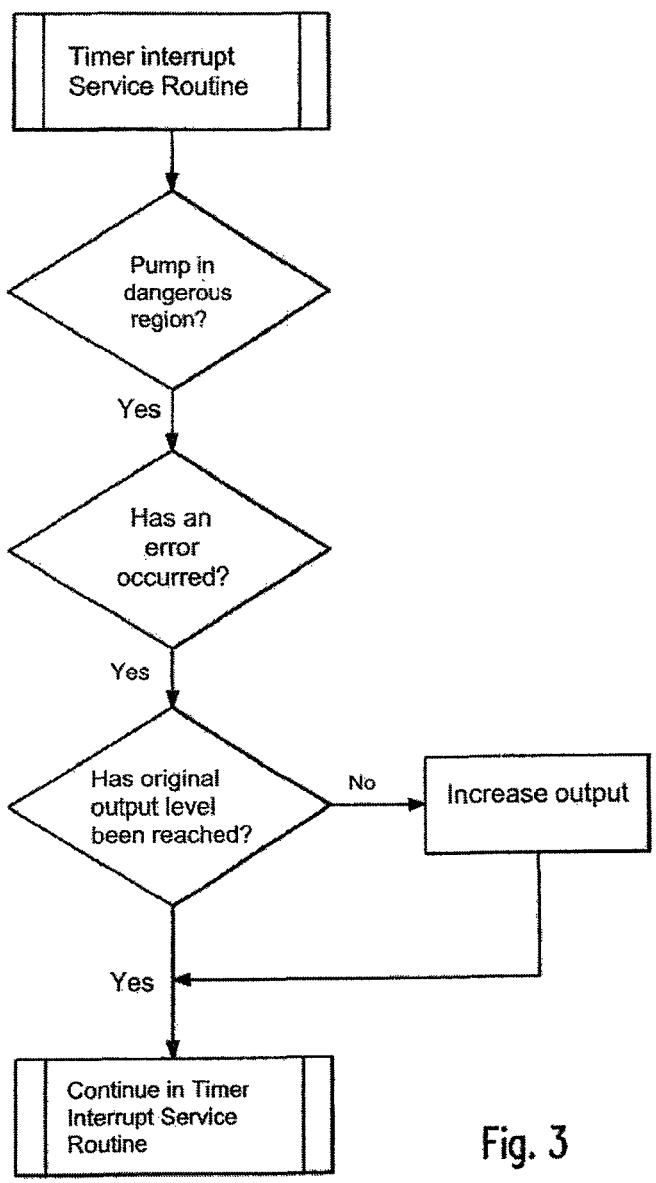
FIG. 3 is a flow diagram to explain the increase of flow rate after a problem has appeared.

In FIG. 1 is a schematic illustration of a rinsing device that comprises a pump 10 with a corresponding electric pump motor and a control device 20 that drives the electric motor of the pump. To measure the current, Imotor, a current-measuring device 11 is provided, which sends a signal indicating the measured current to the control device 20. To input a transport capacity (flow rate) an input device 21 is provided. The control device 20 comprises a microcomputer as well as storage devices for storing the input and measured values as well as for (permanent) storage of limiting values. This is explained below with reference to FIGS. 2 and 3.

The current that the motor of the pump 10 receives is measured continuously by the sensor 11, and a corresponding measurement signal is sent to the control device 20. The latter detects in a first step whether the current exceeds a first prespecified value (level A). If this is not the case, the pump is operated in the usual manner, i.e. in such a way that the motor is operated in order to reach a prespecified transport capacity. If the first prespecified current value is being exceeded, in a second step information is extracted as to whether the current exceeds a second prespecified value that is higher than the first current value. If this is the case, the motor of the rinsing pump is completely switched off, in order to avoid damage. In addition, a warning signal is emitted. If the current does not exceed the second prespecified current value, in a third step information is extracted as to whether the present flow rate exceeds a prespecified limiting value, so that the pump is operating in the dangerous region. If this is not the case, the pump again continues "normal" operation, i.e. the pump motor is operated until the prespecified transport capacity has been reached. However, if the prespecified limiting value of the flow rate has been exceeded, so that the pump is operating dangerously, the flow rate is reduced to a safety value, and hence the rinsing pump is put into a safe operating state. Now the pump is again switched into "normal" operation, in which the motor is controlled so as to reach the prespecified transport capacity. Then the stored control program begins again with the first step.

To ensure reliable operation that is also free of rapid, uncontrolled oscillations, the Timer Interrupt Service Routine shown in FIG. 3 is employed, with interrogation in the following sequence. The first step, again, is to determine whether the pump is in the dangerous region, i.e. whether the limiting value of flow rate has been exceeded. The next question is whether an error has previously occurred, i.e. whether the flow rate was previously reduced to the safety value. If this is the case, has the original output level, corresponding to the prespecified flow rate, been reached? If not, then the output of the pump (corresponding to the motor current) is elevated and the pump is again operated beginning with the first question in the Timer Interrupt Service Routine shown in FIG. 3. If the output level has been reached, the pump continues to be operated in this routine without increasing the output. This routine is followed in a time-controlled manner, so that no increase in output that would cause abrupt, too rapid control oscillations occurs; instead there is a two-point regulation with a fixed switching period.

It will be appreciated by those skilled in the art that changes could be made to the embodiments described above without departing from the broad inventive concept thereof. It is understood, therefore, that this invention is not limited to the particular embodiments disclosed, but it is intended to cover modifications within the spirit and scope of the present invention as defined by the appended claims.

I claim:

1. A method of operating a rinsing pump comprising:
setting or adjusting a rinsing flow rate of a rinsing probe;
detecting an electrical current received by the rinsing pump, wherein the electrical current directly corresponds to a rinsing pressure within the rinsing probe;
comparing the electrical current to a first predetermined current value; and
reducing the rinsing flow rate to a safe flow rate when the electrical current exceeds the first predetermined current value,
wherein the first predetermined current value corresponds to a first predetermined limiting rinsing pressure, and
wherein the rinsing flow rate is reduced to the safe flow rate based only on the comparison of the electrical current to the first predetermined current value, and further comprising:
after reducing the rinsing flow rate to the safe flow rate, increasing the rinsing flow rate at a predetermined rate of increase until a predetermined desired flow rate has been reached.

2. The method according to claim 1, further comprising:
comparing the electrical current to a second predetermined current value, wherein the second predetermined current value is greater than the first predetermined current value; and
turning the rinsing pump off when the electrical current is greater than the second predetermined current value.

3. The method according to claim 2, further comprising:
before comparing the electrical current to the second predetermined current value, comparing the electrical current to an initial predetermined current value, wherein the initial predetermined current value is less than the second predetermined current value.

4. The method according to claim 2, wherein the second predetermined current value corresponds to a second predetermined limiting rinsing pressure.

5. The method according to claim 1, wherein the predetermined rate of increase occurs stepwise.

6. The method according to claim 1, wherein the rinsing flow rate is not separately measured.

7. The method according to claim 1, further comprising:
determining whether the rinsing flow rate was reduced previously.

8. The method according to claim 1, further comprising:
comparing the electrical current to a third predetermined current value, wherein the third predetermined current value corresponds to the predetermined desired flow rate.

9. The method according to claim 1, further comprising:
comparing the electrical current to a second predetermined current value, wherein the second predetermined current value is greater than the first predetermined current value; and
generating a signal when the electrical current is greater than the second predetermined current value.

* * * * *